United States Patent [19]

Adams et al.

[11] Patent Number: 4,809,308

[45] Date of Patent: Feb. 28, 1989

[54] METHOD AND APPARATUS FOR PERFORMING AUTOMATED CIRCUIT BOARD SOLDER QUALITY INSPECTIONS

[75] Inventors: John Adams, Escondido; Juan Amoroso, Jr., San Diego; Paul Axford, La Jolla; Phil Bowles, Encinitas; Mike Juha, Del Mar; Van Nguyen, San Diego; Charles Preskitt, La Jolla; Ed Ross, Escondido; Doug Thompson; Paul Turner, both of San Diego, all of Calif.

[73] Assignee: IRT Corporation, San Diego, Calif.

[21] Appl. No.: 831,997

[22] Filed: Feb. 20, 1986

[51] Int. Cl.$^4$ .......................... G06F 15/46; G06F 5/32

[52] U.S. Cl. ..................................... 378/99; 378/901; 378/58

[58] Field of Search ..................... 378/901, 99, 98, 58, 378/4, 54; 358/111; 364/414

[56] References Cited

U.S. PATENT DOCUMENTS

| | | | |
|---|---|---|---|
| 2,475,596 | 8/1945 | Dawson | 378/58 |
| 3,454,762 | 2/1966 | Vollmer, Jr. | 378/58 |
| 3,889,053 | 6/1975 | Lloyd et al. | 358/106 |
| 4,028,728 | 6/1977 | Sharp | 358/106 |
| 4,064,440 | 12/1977 | Roder | 378/58 |
| 4,344,146 | 8/1982 | Davis, Jr. et al. | 364/552 |
| 4,349,739 | 9/1982 | Annis | 378/58 |
| 4,415,980 | 11/1983 | Buchanan | 378/58 |
| 4,417,353 | 11/1983 | Groh et al. | 378/58 |
| 4,549,306 | 10/1985 | Shideler et al. | 378/58 |

FOREIGN PATENT DOCUMENTS 52-128190 10/1977 Japan.
54-143290 11/1979 Japan.
59-75140 4/1984 Japan.

OTHER PUBLICATIONS

Article "Image Processing Boosts the Power on Non-Destructive Testing", *Electronic Packaging and Production*, Jun., 1985.
Article, "Automated Inspection System Detects Solder Defects Beneath Surface-Mounted Devices", *Blanset Publication*, Jun. 1985.
Advertisement "The IRT Solder Quality Inspection System . . . ", *Electronic Packaging & Production*, Aug. 1985.
"Computer-Controlled Optical Testing of High-Density Printed-Circuit Boards," M. A. West et al., IBM Journal of Research and Development, Jan., 1983.
"Solution of Measuring and Inspection Problems by Gray-Level Image Processing System Implemented with Video and X-Ray Equipment," H. A. Linkenbach et al., Siemens Forschungs-und Entwicklungsberichte, 1984.
"Automatic Inspection System for Printed Circuit Boards," Y. Hara et al., IEEE Transactions on Pattern Analysis and Machine Intelligence, Nov. 1983.

*Primary Examiner*—Carolyn E. Fields
*Assistant Examiner*—Joseph A. Hynds
*Attorney, Agent, or Firm*—Brown, Martin, Haller & Meador

[57] ABSTRACT

A method and apparatus for measuring structural characteristics of a manufactured circuit board containing solder joints by automated real-time digital X-ray radiographic inspection techniques. A circuit board under examination is automatically positioned by a digitally controlled multi-axis positioning system between an electronic X-ray source and an electronic X-ray imaging system. X-rays, in a beam of X-rays from the X-ray source, are directed towards the circuit board. The X-rays are absorbed, scattered and transmitted through the circuit board. The X-rays transmitted through the circuit board are directed upon the X-ray imaging system. The X-ray imaging system converts the transmitted X-rays into digital images which represent the radiographic density of the portion of the circuit board under examination. The digital images are stored within a digital image processor. A computer, under program control, performs calculational measurements on the digital images so as to measure the structural characteristics of the solder joints and components on the circuit board. The calculational measurements are compared to predetermined standards corresponding to acceptable quality standards programmed into the computer. In response to the comparison, the computer provides an accept/reject decision on the circuit board in addition to providing manufacturing process control information for correction of found defects.

21 Claims, 5 Drawing Sheets

METHOD AND APPARATUS FOR PERFORMING AUTOMATED CIRCUIT BOARD SOLDER QUALITY INSPECTIONS

BACKGROUND OF THE INVENTION

I. Technical Field

The present invention relates to automated circuit board inspection systems and techniques. More specifically, the present invention relates to a novel method and apparatus for performing measurements of the structural characteristics of a manufactured circuit board having solder joints thereupon by a fully automatic real-time digital X-ray radiographic inspection techniques.

II. Background Art

In electronics, components are typically mounted upon or inserted into a circuit board. The electrical contact between the circuit board and the components is assured by soldering of the component into permanent position. Thereafter, the electrical integrity of the circuit board depends upon the mechanical integrity of the soldering completed during the circuit board assembly. Soldering processes are well-known and may be reasonably controlled to correct solder related deficiencies. However, soldering processes do not always work perfectly with deficiencies such as solder skips, bridges, insufficient amounts of solder, blow-holes and pin holes which can occur as a result of variations in materials in the solder process. Defects, such as those just mentioned, occur sufficiently often such that it is mandatory to inspect solder connections to reduce solder connection related failures.

Traditionally, solder quality inspection has been performed visually merely because of the fact that humans sense more data visually than with any other of the senses. As a result, previous inspections standards for solder quality were written in terms of the external appearance of the solder connection. The objective of a solder quality inspection is also to insure mechanical integrity of the solder connection. Since mechanical integrity is dependent upon the interior structure of the solder connection, visual inspection techniques are wholly deficient in verifying mechanical integrity.

The mechanical integrity of a solder connection depends upon the type of solder alloy used, the solder connection structure (surface mount versus pin-through-hole) and the presence of an adequate and uniform volume of solder bonding (or wetting) of the electronic component to the circuit board. Visual inspection is regarded as a qualitative test, rather than a quantitative test. In visual inspections, the external appearance of the solder connection is used to infer internal structural integrity. Visual inspections are an accepted solder quality inspection practice used to indentify gross variations in connection structures, such as missing pins, insufficient solder volume, excess solder or bridging. However, visual inspection cannot verify the uniformity of the solder within the connection, and cannot detect defects that are hidden below components mounted on the circuit board. Solder uniformity has a critical influence on the strength and durability of the solder connection. Solder connection strength and uniformity are particularly important in the connection of surface mount devices where the devices are held to the circuit board by the solder connection. It is well-known in the surface mount device art that solder connections are more susceptible to thermal and mechanical stress related failures than pin mounted devices. In solder mounted devices, visually inspected structurally marginal connections, due to solder non-uniformity, may still provide electrical connection without the defect being discovered in stress testing. As a result, the marginal connection or hidden defect is a likely candidate for a long term failure while under normal mechanical and thermal stress. With a greater number of surface mount components being used in circuit boards, visual inspections are proving, in many cases, to be deficient in detecting structural deficiencies in the solder connections.

Solder quality visual inspection systems examine the circuit boards to detect defects such as components missing; components incorrectly oriented; missing or bent component pins or leads such that the component does not make a connection; cracked solder connections; solder bridge between component pins or circuit board pad; small holes present at the surface of the connection; insufficient clearance between component pins; excess solder in the connection; insufficient solder in the connection; solder spurs, spikes, balls or splashes; poor solder wetting on the board or the component; a misshaped solder connection which indicates surface tension problems; component askew pads on the circuit board; component pins lifted or tilted from the circuit board; component pins misaligned with circuit board pads; and component pins not projecting through the circuit board hole. Each of the above defects indicate conditions that can compromise the electrical and mechanical integrity of the circuit board.

In many applications, defects are hidden from the human eye or machine vision inspection systems. An example of such a defect is in the case of solder porosity or voids. While defects may not be masked by visual barrier, increasing circuit density may result in defects which are not readily apparent to the human eye at production line rates. With machine vision inspection systems, inspection deficiencies still exist. For example, machine vision inspection systems would be unavailable for inspecting defects such as solder balls under a pin grid array.

Typical inspection systems are oriented toward finding defects rather than avoiding the defects in the production of future items. The avoidance of defects essentially requires rapid process control feedback from the inspection system to the production line. Process control feedback of the defects requires quantitative analysis feedback of the deficiencies and providing this information to the production line to control the soldering process. For example, quantitative quality data such as the excess amount of solder volume present in a solder connection must be fed back to the soldering process to reduce the solder used in future units so as to eliminate the defect. The present human and machine vision inspection systems lack the ability to provide quantitative data for feedback control to the process lines for correcting process deficiencies. With faster production lines, inspection systems must detect process drift before the production line turns out numerous defective items. For solder quality process control, the inspection accuracy and repeatability needed must detect even the smallest changes in solder connection before they grow to become defects.

SUMMARY OF THE INVENTION

In the case of solder quality inspections, the use of X-ray inspection techniques enables the inspection of visually hidden defects. X-ray imaging and computer-based image processing are well suited for solder quality inspections. The metallic alloys used in solder are remarkably opaque to X-rays as compared to the translucence of the ceramics, epoxies, silicon or copper materials used in circuit board assemblies. In addition, the ceramics, epoxies, silicon or copper materials have differing degrees of translucence so as to permit the distinction between these materials. As a result, small defects in the solder or the circuit board are readily identified. The penetrating nature of X-rays is particularly suited for searching out hidden defects with respect to solder connections due to contrast between solder and other circuit board materials and components. X-ray inspections may be utilized to perform quantitative measurements in quality assurance inspections of solder connections. The strength of X-ray inspection is in the ability to display the external and internal structure of each solder connection. In effect, X-ray inspection images are three-dimensional, i.e. length, width and thickness with length and width (or size) being represented by object contrast from surrounding areas with thickness being represented by the shades of gray or black. With data corresponding to the size and thickness of a solder connection, a determination can be made as to the quality of the solder connection.

The present invention is a fully automated X-ray solder quality inspection system and a method for performing solder quality inspections utilizing X-rays.

In summary, the present invention is a method and apparatus for measuring structural characteristics of a manufactured circuit board containing solder joints by automated real-time digital X-ray radiographic inspection techniques. A circuit board under examination is automatically positioned by a digitally controlled multi-axis positioning system between an electronic X-ray source and an electronic X-ray imaging system. X-rays, in a beam of X-rays from the X-ray source, are directed towards the circuit board. The X-rays are absorbed, scattered and transmitted through the circuit board. The X-rays transmitted through the circuit board are directed upon the X-ray imaging system. The X-ray imaging system converts the transmitted X-rays into digital images which represent the radiographic density of the portion of the circuit board under examination. The digital images are stored within a digital image processor. A computer, under program control, performs calculational measurements on the digital images so as to measure the structural characteristics of the solder joints and components on the circuit board. The calculational measurements are compared to predetermined standards corresponding to acceptable quality standards programmed into the computer. In response to the comparison, the computer provides an accept/reject decision on the circuit board in addition to providing manufacturing process control information for correction of found defects.

It is an object of the present invention to provide a novel and improved fully automated real-time X-ray radiographic solder quality inspection system and method for measuring the structural characteristics of solder joints on circuit boards.

It is yet another object of the present invention to provide a method and apparatus for performing X-ray radiographic inspections of circuit board solder connections and providing decisions based on preprogrammed instructions for the acceptance or rejection of a circuit board under test while providing data feedback to a solder process production line.

It is a further object of the present invention to provide a method and apparatus for performing X-ray solder quality inspections utilizing a motion processor controlled multi-axis positioning system for permitting the collection of multiple view X-ray imaging data and providing calculational measurements upon the multiple view image data by computer under preprogrammed instructions for determining structural defects, including solder quality defects, in manufactured circuit boards.

It is still a further object of the present invention to eliminate preprogramming by having the inspection machine accept circuit board specification from another computer and automatically devise the sequence of motions and tests required to inspect the particular circuit board type.

BRIEF DESCRIPTION OF THE DRAWINGS

These and other objects, features and advantages of the present invention will be more fully apparent from the detailed description set forth below taken in conjunction with the drawings in which like referenced characters identify corresponding throughout and wherein.

DETAILED DESCRIPTION OF THE PREFERRED EMBODIMENTS

Figure 1:
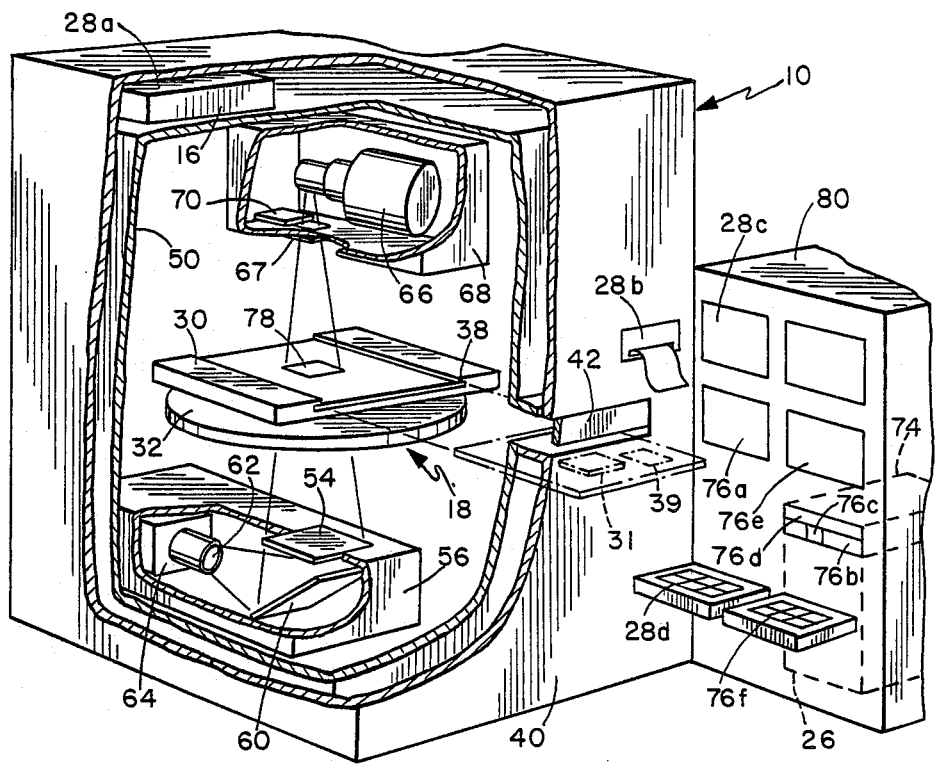
FIG. 1 is a perspective view of an X-ray inspection system of the present invention.
Figure 2:
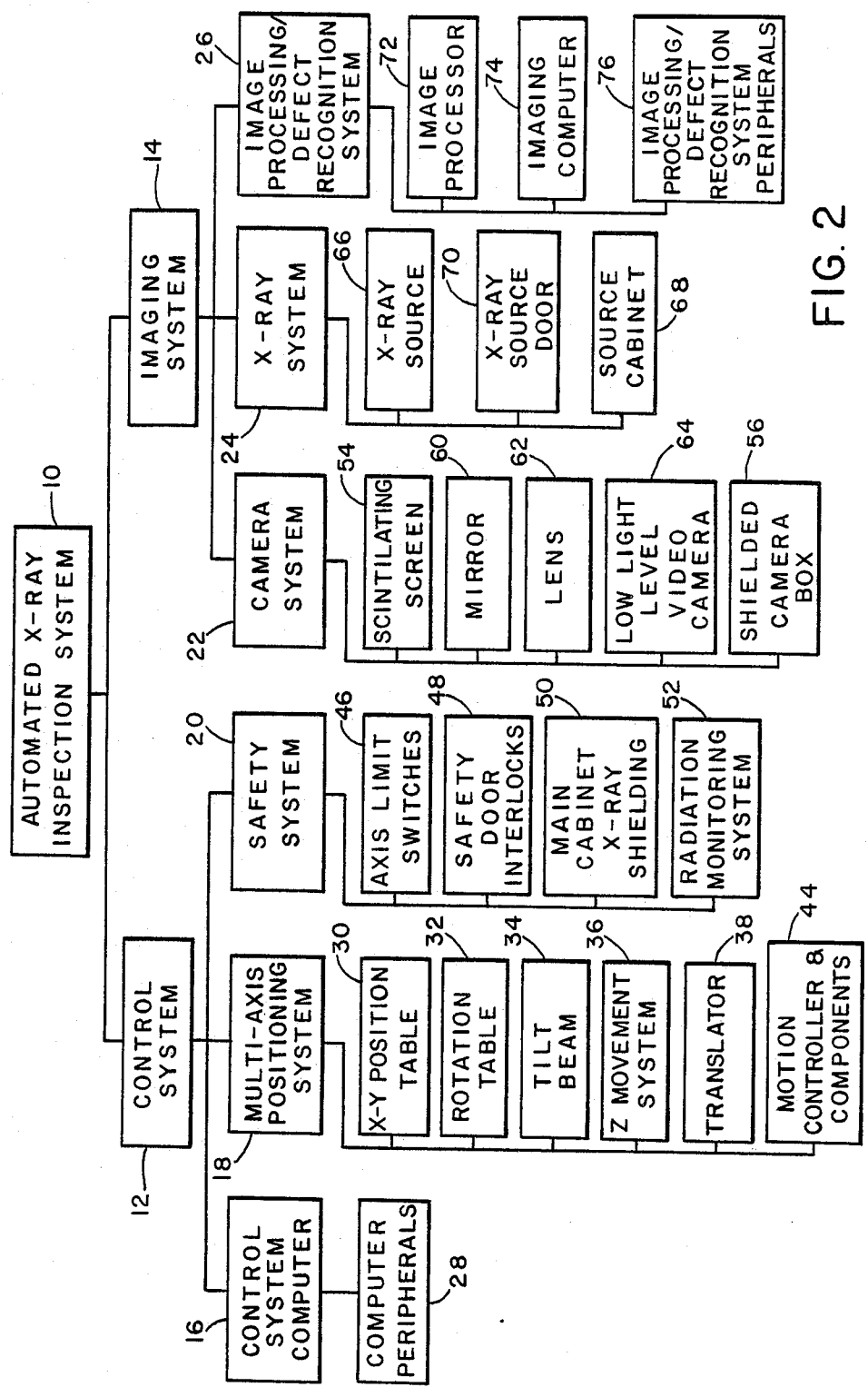
FIG. 2 is a block diagram of the major components of the system of FIG. 1.

The present invention is an automated real-time circuit board solder quality inspection system which uses digital X-ray radiographic imaging techniques and a rule-based defect recognition system. Referring to FIGS. 1 and 2, FIG. 1 illustrates a perspective view of the major component layout while FIG. 2 illustrates in block diagram form the major components of the system. In FIGS. 1 and 2, the automated X-ray circuit board solder quality inspection system 10 includes a control system 12 and an imaging system 14. Control system 12 is comprised of three major systems, control system computer 16, multi-axis positioning system 18, and safety system 20. Imaging system 14 is comprised of three major systems, camera system 22, X-ray system 24 and image processing/defect recognition system 26.

In control system 12, control system computer 16 is a digital computer which has computer peripherals 28 associated therewith. Computer peripherals 28 include such equipment as data storage system 28a, printer 28b, display monitor 28c, and keyboard 28d and an interface with the multi-axis positioning system 18 and safety system 20 along with an interface to the image processing/defect recognition system 26 and x-ray 24. Also included are interfaces to external computers and/or robots.

Also included in control system 12 is multi-axisw positioning system 18. Multi-axis positioning system includes an x-y positioning table 30 which permits movement of a circuit board mounted therein in a horizontal plane. The x-y positioning table 30 is mounted upon a rotation table 32 which permits 360 degree rotation of the x-y positioning table 30. Rotation table 32 and x-y positioning table 30 and translator 38 may be generically defined as a motion table which is mounted upon a tilt beam 34 which permits tilting of the motion table in an angled plane to the horizontal plane. A z movement system 36 permits movement of the motion table assembly in a vertical direction. A translator 38 is utilized to move a circuit board mounted upon x-y positioning table 30 to and form a position adjacent to an exterior wall of cabinet 40 at the load/unload door 42 to a central position within cabinet 40. A motion controller and components 44 receives the control signals from the control system computer 16 and provides the appropriate electromechanical movement within the multi-axis positioning system.

A safety system 20 includes axis limits switches 46, safety door interlocks 48, cabinet X-ray shielding 50, and radiation monitoring system 52. Axis limit switches 46, safety door interlocks 48, and radiation monitoring system 52 provide status information signals with respect to the multi-axis positioning system 18, the position of the load/unload door 42, and the level of radiation at selected locations within and about the X-ray inspection system. Safety system 20 is provided for both operator safety and equipment failure protection.

In imaging system 14, camera system 22 is mounted within cabinet 40 beneath the motion table assembly. Camera system 22 includes a fluorescent or scintillating screen 54 mounted in the upper wall of lead shielded camera box 56. Mounted within camera box 56 is mirror 60, lens 62, and low-light-level video camera 64.

X-ray system 24 is also mounted within cabinet 40 and is comprised of an electronic X-ray source 66 and X-ray spectrum filter 67 mounted within a X-ray source cabinet 68. Cabinet 68 includes an electrically actuated mechanical X-ray source cabinet shutter 70 mounted at a lower wall of cabinet 68. Source 66 generates a beam of X-rays that exit through an opening in the lower wall of cabinet 68. X-ray spectrum filter 67 modifies the X-ray energy spectrum in such a way that adjusts the sensitivity of the system to the component under inspection. X-ray source door 70 when in the closed position cuts off the beam of X-rays emanating from cabinet 68 by covering the opening.

Included with imaging system 14 is image processing-/defect recognition system 26. Image processing/defect recognition system also includes a digital image processor 72 and an imaging computer 74. The image processor 72 includes at least three image memories, also called frame buffers. System 26 includes peripheral devices 76 such as an image display monitor 76a, streaming tape drive or optical disk 76b, flexible disk drives 76c, hard disk 76d, image display monitor 76e, keyboard 76f, and joystick controller 76g.

Referring to FIG. 1, the components of FIG. 2 are illustrated in their structural cooperation. Inspection system 10 is controlled by control system computer 16 which is mounted within main cabinet 40 but external to the main cabinet X-ray shielding 50 located within main cabinet 40. Control system computer 16 controls the operation of the multi-axis processing system 18 and additional devices such as the load/unload door 42 and the X-ray source door 70. Control system computer 16 is also responsible for reporting results of a board test through BOARD ACCEPTED and BOARD REJECTED and status lights (not shown). Control system computer 16 includes a data storage system such as hard disk 28a mounted within computer 16. Data storage system 28a is used for storing circuit board inspection programs and inspection result data. Also associated with computer 16 is a printer 28b which prints defect tags for individual boards and summary reports for board lots. Computer 16, also includes, mounted in an operator console cabinet 80 a display monitor 28c which displays control status information and messages regarding system operation and a keyboard 28d or any other input means which may be included to provide operator inspection control of a circuit board. Imaging computer 74 and computer 16 are interfaced with the other so as to communicate over a common bus. Computer 16 also continuously monitors various sensors so as to detect system faults from indicators such as are included within safety system 20.

An electronic X-ray source 66, which generates a continuous beam of X-rays of an energy level of about 160 Kev, is mounted within lead shielded X-ray source cabinet 68. To provide a continuous and stable source X-ray level, X-ray source 66 operates with an anode current of 0.2 mA. One type of X-ray source is disclosed in U.S. Pat. No. 4,521,902. Source cabinet 68 is positioned in an upper portion of cabinet 40 and includes a source X-ray door 70 which permits, when open, a beam of X-rays, which may be collimated to improve image quality, to project downwardly and outwardly through an X-ray source door opening in cabinet 68.

Mounted beneath cabinet 68 is the motion table which is comprised of x-y positioning table 30, rotation table 32, and translator 38. For purposes of clarity in FIG. 1, tilt beam 34 and z movement system 36 are not shown in structural form and may be implemented in many forms by one skilled in the art. When a circuit board 78 is mounted on the motion table and is undergoing examination, the beam of X-rays is projected towards a portion of circuit board 78 and an opening in the motion table. The X-rays transmitted through the circuit board 78 are directed towards lead shielded camera box 56 which is mounted at the bottom of cabinet 40 within shielding 50. Mounted in an upper panel of box 56 is fluorescent or scintillating screen 54. Mounted beneath screen 54 is an aluminized front surface mirror 60 mounted at a 45 degree angle to a horizontal plane. Also mounted within box 56 is low-light level video camera 64 which has a lens 62 disposed between camera 64 and mirror 60.

In the operation of the inspection system, the translator is positioned adjacent to the load/unload door 42 for receiving, within a fixture thereupon (not shown) adapted for holding a particular circuit board type, circuit board 37. Also mounted upon translator 38 is step wedge 39 which is a section of varying thicknesses of stainless steel. Step wedge 39 is utilized in the image processing as a known reference (a known density) by which gray levels of an acquired image may be referenced so as to account for drift in the X-ray source output. The step wedge as a reference may also be used to calibrate the X-ray source to a specific output. Upon initialization of the system by the operator, such as by control pushbutton switches (not shown) or the closure of load/unload door 42, the translator 38 is moved to position the circuit board directly beneath the X-ray source door opening of cabinet 68.

The inspection routine is directed by image processing/defect recognition system 26 which includes a main inspection program for computer 74. Programmed into imaging computer 74 through the peripheral devices or by downloading from another computer system is data such as view location, device type, pin number, etc. along with the selection of image inspection algorithms from a library of algorithms stored within imaging computer. Computer 74 instructs control system computer 16 to move the motion table during the inspection period and open X-ray source door 70 during the inspection and closing a X-ray source door 70 upon completion of the inspection. When the X-ray source door is opened, a beam of X-rays is projected towards an area of the circuit board ranging in size up to about two and one half inches square.

The circuit board is moved about by the motion table under control system computer control 16 to reach a selected view for inspection. The motion table may be moved through a horizontal plane in an x-y direction along with being rotated, tilted, or moved in a vertical direction toward or away from the X-ray source (so as to provide an imaging zoom feature).

A beam of X-rays projected upon the circuit board results in some photons scattering about the board within cabinet 40 which are absorbed by cabinet shielding 50. Another portion of the X-ray beam is absorbed by the circuit board and solder connection. Yet another portion of the X-ray beam is transmitted through the circuit board where it impacts upon fluorescent or scintillating screen 56 which is positioned in-line with the X-ray beam.

The X-rays impacting upon the fluorescent or scintillating screen are converted into a visible light image. The visible light image of the X-ray shadow image created by the transmission of the X-ray beam through the circuit board is reflected by a flat planar mirror mounted at an angle 45 degrees to the horizontal. The X-ray shadow image appearing at fluorescent or scintillating screen 54 is reflected at a 90 degree angle through lens 62 and into camera 64. The use of a mirror in the system enables the camera to remain outside of the X-ray beam. The analog output of video camera 64 is provided to image processing/ defect recognition system 26.

During the imaging of the circuit board, the analog output of the camera may be displayed upon an image display monitor 76a as a 512×480 pixel image for operator viewing. System 26 includes a high-speed gray scale image processor which digitizes each image pixel into an eight-bit code which corresponds to one of 256 shades of gray. In the gray scale, 0-255, the darker, or denser, the material absorbing the X-ray in the form of a shadow, the lower the gray scale number. Lighter areas in which the X-rays are transmitted through the circuit board, by absorbing less X-rays, have higher gray level numbers.

Image processing/defect recognition system 26 imaging computer 74 performs a multiframe average of the digitized image and stores it within an image (frame buffer) memory. Imaging computer 74 performs computational measurement upon the image during the movement of the motion table to a new view position or the load/unload position adjacent to the load/ unload door. During the movement of the board to the unload position under the control of control system computer 16, imaging computer 74 processes all previously computed measurements by performing analysis on the image measurement data and directs the control system computer 16 to store and output the results.

Figure 3A:
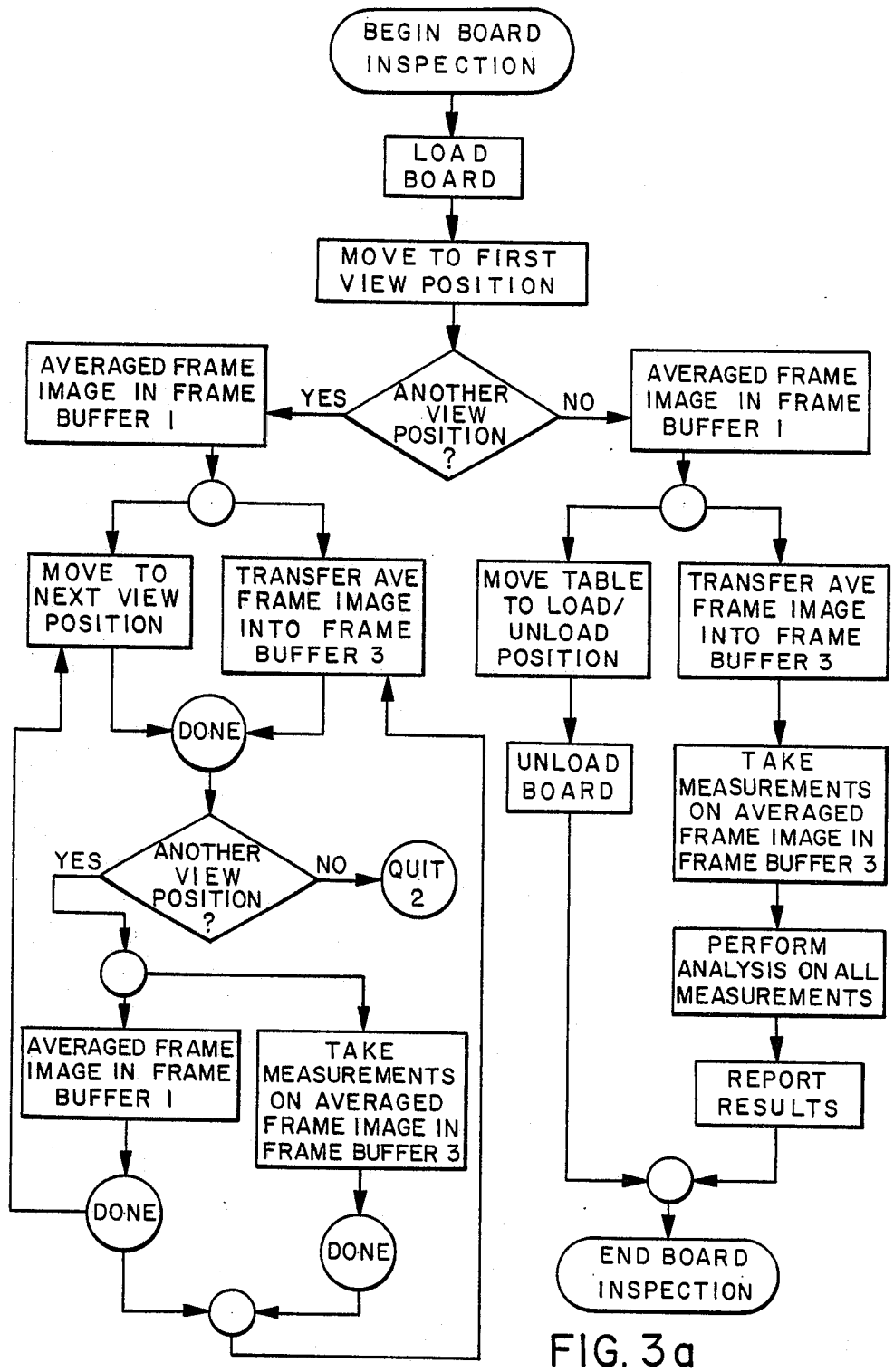
FIG. 3 is a flow chart of the operation of the system FIGS. 1 and 2.
Figure 3B:
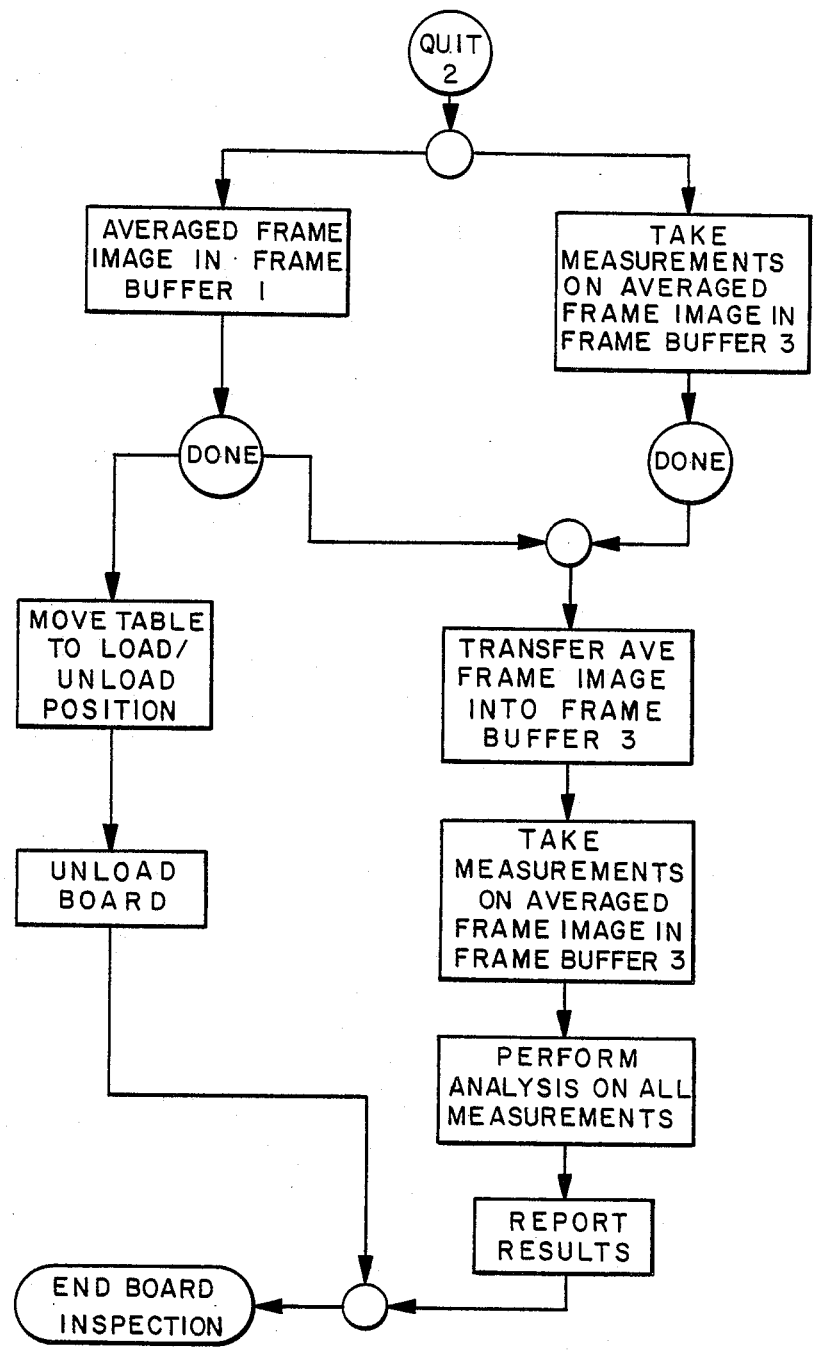

FIG. 3 illustrates a flow diagram of the operation of the inspection system. At the beginning of an inspection cycle, the X-ray source door is closed with the translator in the load/unload position adjacent the load/unload door. The control system computer begins an inspection cycle after a circuit board has been loaded onto the motion table and the operator has initialized the inspection cycle. The control system computer instructs the translator to position the circuit board beneath the closed X-ray source door . After the load/unload door has been closed by the operator, the control system computer sends to the image processing/defect recognition system identifying information as to the type of circuit board that is to be inspected. The control system computer may typically obtain this information, such as circuit board type and lot, from a bar code imprinted on the circuit board and read by a bar code scanner. Alternatively this information may be provided by an operator through the operator's keyboard or by a message from an external computer.

The imaging computer uses this information to select portions of a main inspection program that are applicable to the type of circuit board to be inspected. Each circuit board has a circuit board specific inspection list associated therewith. Each inspection list contains view information used by the main software module, Inspection List Interpreter (ILI), within the imaging computer for instructing the control system computer in motion control activity. The specific inspection list is also used by another software module, Image Measurement Module (IMM), within the imaging computer for taking measurements on the image. Other software modules within the imaging computer are a Results Interpreter Module (RIM), a Blackboard Interface Module (BRIM), and a Blackboard. Each circuit board type will be inspected with different views and different sets of measurement and analysis routines. Hence, each circuit board type has a specific IMM, RIM, BRIM, and Blackboard structure.

The primary responsibility of the IMM is to take measurements from the image data and place the measurements on the Blackboard. To perform these measurements the IMM contains pre-defined measurement routines or algorithms specified by the inspection list for each joint. These algorithms are selected from a library of algorithms which includes algorithms for all joint types.

The primary responsibility of the RIM is to analyze the measurement data placed on the Blackboard by the IMM. The RIM contains pre-defined analysis routines that correspond to the measurements specified in the inspection list for each joint. Based on the analysis of the measurements, the RIM places on the Blackboard the results of the measurement analysis as to which pins were defective and the type of defect.

The BRIM is responsible for providing the defect data placed on the Blackboard by the RIM to the control system computer for reporting of the defect to the operator.

The Blackboard is merely a temporary data storage medium by which the IMM, RIM and BRIM store and retrieve data in communicating with another module.

Returning to the inspection system operation, when both have acknowledged to the other that each is ready to begin the inspection, the imaging computer instructs the control system computer to move the motion table to the first view position. Since a view position table associated with each circuit board type is contained within a control system computer memory, the imaging computer need send only a "move to position" command. The view position table, created previously for the particular board type, contains the axis values for each defined view. As a result, when the control system computer receives a "move to position" command, it uses the values from a local view position table stored therein to provide control signals to the motion controller.

Upon completion of the move to the first view position, the imaging computer instructs the control system computer to open the X-ray source door to permit the beam of X-rays to be directed through the circuit board to the camera system. Also upon completion of the move to the first view position, the imaging computer, based upon the programmed instruction list, determines whether there is another view position following the present view position or whether the present position is the last view position that an image is to be acquired and measured. This data is transferred to the control system computer for controlling the motion table's next move to either a new view position or the load/unload position.

The next event in the inspection cycle is the taking of a multiframe average of the X-ray image of the first view provided by the image processor. The averaging of the frame image is taken on all views. The average frame image data are stored within the imaging system computer in a memory, frame buffer one. During the averaging of the frame image data on the first view position image, no measurements on the averaged frame image data are performed. After the frame average is taken, the imaging computer instructs the system control computer to close the X-ray source door so as the cut off the X-ray beam directed towards the circuit board.

In the condition there is another view to be taken, the imaging computer instructs the control system computer to move the motion table to the next view position. Simultaneously, the imaging computer transfers the previous view averaged frame image data from frame buffer one to another memory, frame buffer three.

Upon completion of the moving of the motion table to the new view position and the transfer of the average frame image data to frame buffer three, the imaging computer again determines whether or not the present position is the last view position. Should there be another view position, the X-ray source door is opened and averaged frame image is computed and stored into frame buffer one. Simultaneously, measurements are taken on the averaged frame image data stored in frame buffer three. Upon completion of the acquisition and storage of frame average into frame buffer one, the X-ray source door is closed and the motion table is moved to the next view position. Upon completion of both the frame average into frame buffer one and the measurements on frame buffer three, the previous averaged frame image data stored in frame buffer one is transferred to frame buffer three. Should another view be programmed into the inspection list, the sequence of just described events is repeated. It should be noted that by opening the X-ray source door only during the acquisition of the frame averaged image, minimal exposure of the circuit board to the X-ray beam is achieved.

However, should there not be a view following the present view, the inspection cycle goes into a QUIT mode. In the QUIT mode, the present averaged frame image data is stored into frame buffer one while measurements are made on the data stored in frame buffer three. Upon completing the computation of the averages of the present frame image data and storage into frame buffer one, the motion table is moved to the load/unload position for unloading of the circuit board.

Upon completion of both the frame average into frame buffer one and the measurements taken on the averaged frame image data stored in frame buffer three, the averaged frame image from the last view is transferred from frame buffer one into frame buffer three. Once the last view data is in frame buffer three measurements are taken upon the data. Upon completion of the measurements on the last view data, the imaging computer performs a defect analysis on the data collected from all prior measurements. The results of the analysis are prepared and transferred to the control system computer for reporting. If any defects were found, a defect tag is printed through the printer associated with the control system computer. The defect tag indicates the location of the defect and the defect type. If no defects were found on the circuit board then no printout is provided. The system may be provided with "BOARD REJECT" and "BOARD ACCEPT" lamps which indicate the status of the board upon completion of the test. The control system computer keeps two counts for statistical purposes along with all the defect records for each lot of boards. The counts are a running tabulation of the number of circuit boards "accepted" and "inspected". Once the motion table is returned to the load/unload position and the circuit board has been unloaded, the system is ready to begin another inspection cycle.

Still referring to FIG. 3, if after the imaging computer instructs the control system computer to move the motion table to the first view position and it is determined that no further view positions are required, the X-ray source door is opened, an averaged frame image is taken and stored in frame buffer one. Upon storage of the average frame image data in frame buffer one, the X-ray source door closes and the motion table is moved to the load/unload position for subsequent unloading of the circuit board. Simultaneously, the averaged frame image data is transferred to frame buffer three where measurements are taken on the averaged frame image data. Upon completion of the measurements, the imaging computer performs an analysis of all of the measurements in the view so as to detect defects. The results of the defect analysis are transferred to the control system computer for generating the appropriate report and operator status indications. After the reports have been generated and the circuit board removed from the motion table, the inspection cycle is completed.

An inspection list is associated with each type of circuit board to be tested. The inspection list is generated either by an operator who generates the inspection list in accordance with the inspection parameter requirements or inspection data may be downloaded from a computer-aided design (CAD) system and the inspection list generated automatically by the computer. An inspection list for each type of board to be inspected is stored within a storage medium in the imaging computer with the corresponding view position coordinate list stored within the control system computer.

Figure 4:
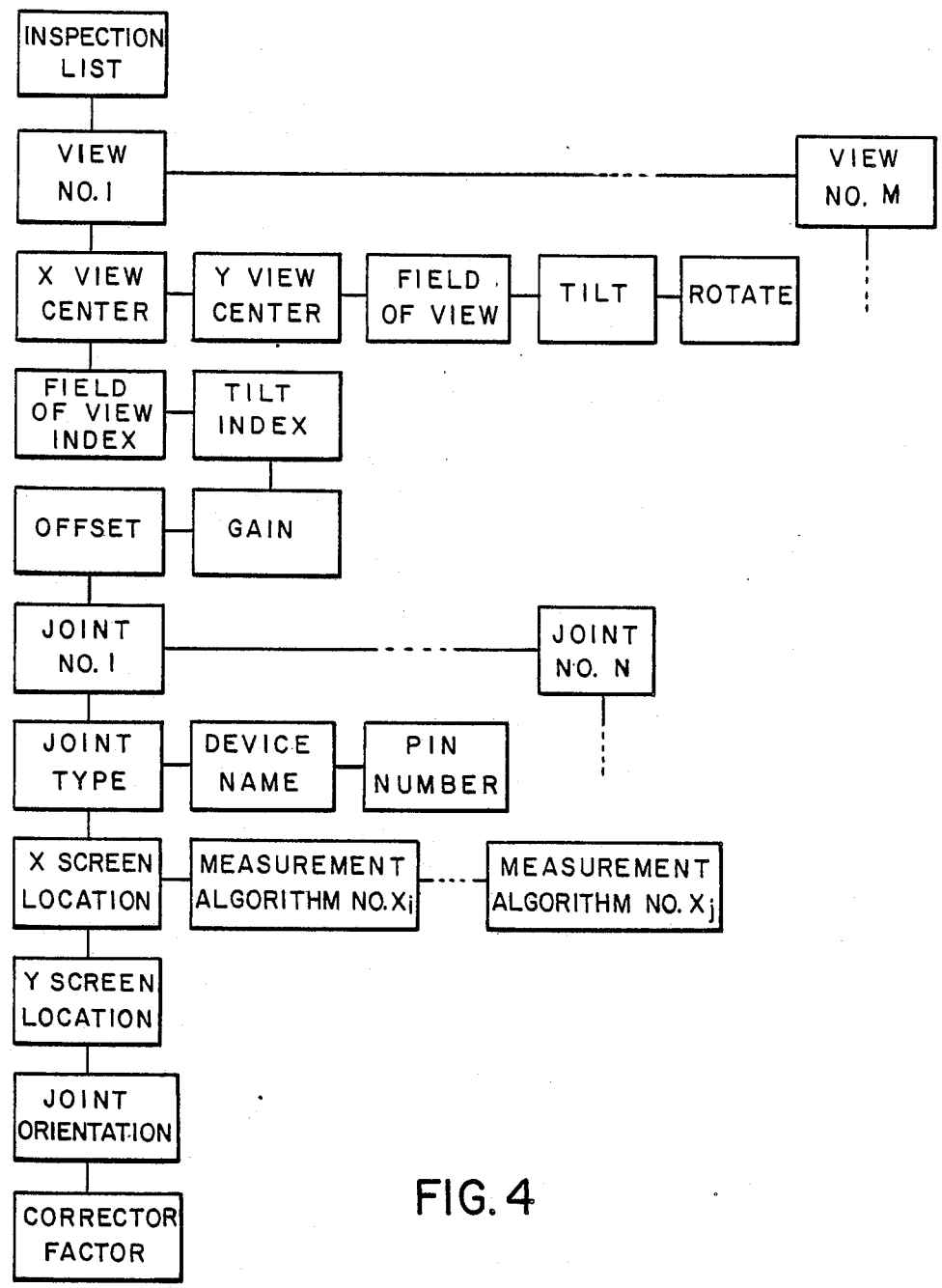
FIG. 4 is a block diagram of the inspection list program.

FIG. 4 illustrates an exemplary flow chart of a typical inspection list. The inspection list is comprised of a single view or a series of views and, as illustrated in FIG. 4, includes view numbers 1 through M. Each view number contains inspection instruction data for acquiring and analyzing image data. The view number is an integer which labels a view subtree wherein the view subtree contains the axis values of the motion table. The constituents of the axis values are the x, y, field of view or zoom axis, tilt and rotate coordinates. The view subtree is essentially structured as a sublist of the view number.

In the view subtree the x view center is the x axis displacement from a home or zero position on the motion table. The selected x coordinate is positioned in the center of the field of view. The y view center is the y axis displacement from the home position on the motion table. The selected y coordinate is also positioned in the center of the field of view.

The field of view is the horizontal length of a plane perpendicular to the field of view or zoom axis which is projected on to the image display monitor as measured from the left edge to the right edge of the monitor screen.

The tilt value is the absolute tilt angle value measured in 1/10th of degrees ranging from 0 to 45 degrees in a horizontal plane. The rotate coordinate is the absolute rotate angle measured in 1/10th degrees of rotation ranging from 0 to 360 degrees from an initial 0 degree angle.

The field of view index is an integer assigned to a specific field of view value. This is used to select parameters depending upon the field of view for inspections. A tilt index is an integer assigned to a specific tilt value and is used to select parameters depending upon the tilt for inspections.

Gain and offset values are used for enabling the best image for each view to be acquired. The gain determines the amount of contrast that the video camera displays on the image display monitor. By increasing the gain, the image appears lighter. By decreasing the gain, the image appears darker. Offset is the amount of brightness that the video camera displays on the image display monitor. An increase in offset makes the image appear darker. A decrease in offset makes the image appear lighter.

Associated with each view there are a series of joint numbers 1 through N with each joint being given an integer identifying number. The joint number is an index to the pin file associated with the inspection list which contains information about the pin. An actual joint typically consists of a bottom pad, barrel and top pad with a pin running through the middle of the pads and barrel. However, a joint in the inspection list is simply an area that is to be inspected so that it may be either a solder joint, a capacitor, a calibration position, a device, or any other area on the circuit board.

Each joint number within a view includes a joint subtree which contains information about the joint. This information includes the joint type, device, name, pin number, x and y screen location, measurements algorithms, joint orientation and correction factors.

A joint type is entered into the sublist as an integer which represents the classification of the joint. This information is used to select inspection parameters which are dependent upon the joint characteristics, such as pad size. The device name is also included using the manufacturer's character abbreviation, which typically stands for the type of electrical component. A pin number is assigned as an integer value associated with the order of the pins on the device. The device name and pin number are useful information when a defect is discovered so that the control system computer will provide a specific component name and pin number in the defect tag printout.

The x screen location is defined as the horizontal displacement of the cursor from the original upper left hand corner of the image display monitor. This location is measured in pixels from 0 to 511 going across the image monitor from left to right. The y screen location is the vertical displacement of the cursor from the original upper left hand corner of the image monitor. This location is measured in pixels from 0 to 479 going downward in the image display monitor.

The joint orientation is an integer value which represents the direction of a pin with respect to the image monitor. This value is used in the selection of inspection parameters used which are dependent upon the joint orientation. For example the three o'clock position on the monitor may be assigned an integer value 1 with the six o'clock position on the monitor corresponding to 90 degree rotation and is assigned the integer value 2. Continuing in a clockwise notation system, the nine o'clock position corresponds to 180 degree rotation with the assigned integer value 3 and the twelve o'clock position corresponding to a 270 degree rotation with an assigned integer value of 4.

Most important in the joint sublist are the measurement algorithms associated with each joint number. An integer identifies the algorithm from a library of algorithms (discussed later) which are used to perform image measurement and defect analysis. The results of the defect analysis are used to flag defects found in the image. For purposes herein, the algorithms are numbered for joint number 1 as being algorithm numbers $x_i$ through $x_j$. A correction factor may be included as an integer value which would provide "local joint effects" information to an algorithm. It would allow an algorithm to be adjusted on a per joint basis. For example, an integer value would be used to inform the algorithm that a structure blocks the view of a joint.

In the algorithms used to determine a defect, the imaging computer uses a "rule-based" approach with a set of rules defining what a good feature and a bad feature are for parameters automatically measured by the system. The rules define what an acceptable solder connection is and what constitutes a connection that is defective. For each type of joint a set of parameters or thresholds for various solder-joint characteristics are defined. These parameters may be quickly adjusted by the user, although such adjustments are often not needed. Thickness, density and shape of the solder connections are determined by using the measurement algorithms and comparing the results of the measurements to pre-established criteria. Utilizing the measurement algorithms and analysis algorithms, a library of inspection routines for standard electronic component packages and configurations may easily be created. While some components may require certain measurement and comparison algorithms, others may not. Certain component packages are susceptible to known solder connection defects such that the algorithms may be readily chosen and placed appropriately into the inspection list.

Figure 5A:
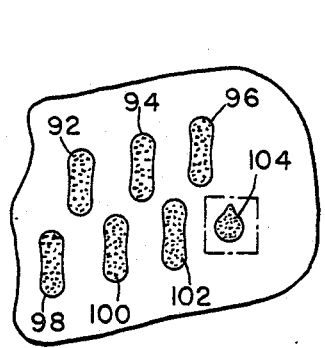
FIG. 5 depicts the imaging of the selected solder connection defects.

FIG. 5 represents three imaged circuit board defects with FIG. 5a illustrating insufficient solder in a through-hole beneath a pin-grid array. In FIG. 5a barrel solder connections 92, 94, 96, 98, 100, 102, and 104 are illustrated. In this defect condition, exemplified by barrel solder connection 104, a cavity exists in the barrel solder connection. The setup requirements for providing the best possible imaging and recognition of this defect requires a large tilt in the motion table. In the measurement algorithm, the minimum and maximum gray values, of a gray level pixel population 2 or more, are calculated. The average gray level in the barrel is calculated and normalized against a step wedge imaged gray level. If the difference between the minimum and maximum gray levels is greater than a predetermined threshold programmed into the machine or the average gray level exceeds a second threshold than a defect exists. In theory, a large difference between the minimum and maximum gray level values in the barrel indicates porosity, voids or blow-holes. A high average alone indicates a more uniform lack of solder, many voids, blow-holes or no solder at all.

Figure 5B:
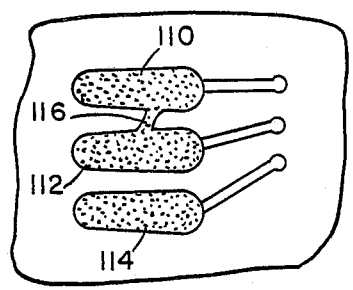

FIG. 5b illustrates a surface mount device (SMD) where bridging, solder forming an unintended conductive path between solder joints and devices has occurred. The motion table is typically setup to detect solder bridging in a SMD with a 1-inch field of view and no tilt angle. This defect is illustrated in FIG. 5b where pads 110, 112 and 114 are shown. There exists in FIG. 5b a solder bridge 116 between pads 110 and 112. For the inspection, a 1-inch field of view and no tilt angle are the typical set up requirements. Two tasks are typically performed to verify whether a defect is present. Given the centroid of the joint, the normalized black count between joints (A) is greater than a threshold then a bridge exists. The second task is checks for the presence of an edge between joints and if an edge is found then a bridge exists.

Figure 5C:
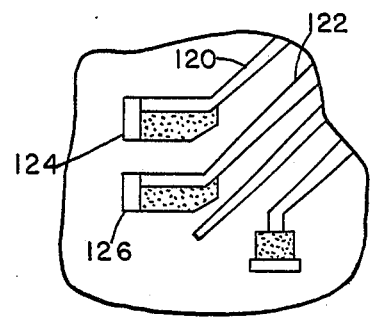

FIG. 5c illustrates a J-leaded surface mount device (SMD) wherein the misalignment of the pins or leads 120 and 122 are respectively offset from the solder pads 124 and 126. If the leads 120 and 122 were properly aligned they would be respectively superimposed over pads 124 and 126 in the image. As a result, there would be no separation in the image of the leads and pads. In this defect condition a component is typically askewed so that the leads are not centered on the pads. The algorithm for measuring the defect condition uses a given centroid of the pin with the centroid of the pad being computed. The shift in centroid of the pin and pad are measured (A). The total shift over the row of pins is next computed (B). Next the number of pins offset in a row are computed (C). A pin is offset if (A) is greater than a first threshold. A device is offset if (B) is greater than a second threshold or (C) is greater than a third threshold.

A solder bridge in typical throughhole solder connections is defined as solder that has formed an unintended conductive path between solder joints is considered a bridge defect. Spikes/icicles (not shown) are non-conductive paths of solder extending beyond the pad. This defect may occur on the top or bottom pad or around the lead and always extends beyond the pad. To detect a solder bridge or spike/icicle a circular profile of pixel data around the joint pad is gathered, excluding any known device interference. The data is filtered using a median filter. A defect exists if the differential along the profile varies more than a rule-based threshold.

In identifying the particular type of defect, the average gray level of the joint ($J_a$) is calculated. The angle of the defect from the position in the profile is next calculated. This is accomplished by scanning outwardly from the joint pad, at the found angle, by following the path of the lowest gray level until the gray level rises above a threshold or a fixed distance is covered. The path length is recorded as the defect length ($D_l$). The algorithm next calculates the average gray level of the defect ($D_a$) centered at the end of the path with the same area dimensions as used to calculate the joint average ($J_a$). From the point along the path where the lowest gray level was found, the algorithm scans plus or minus 90 degrees so as to form an arc from the joint center and following the path of the lowest gray level until the gray level rises above a threshold or a fixed distance is covered. The sum of the path is recorded as the defect width ($D_w$). If the defect length ($D_l$) is greater than a threshold and the average gray level of the defect minus the average gray level of the joint ($D_a - J_a$) is less than a threshold then the defect is a bridge. Otherwise, if the defect length ($D_l$) is greater than a minimum threshold and the defect width ($D_w$) is greater than a minimum threshold, then the defect is a spike/icicle. Since bridges, spikes/icicles will appear as protrusions emanating from the pad edge, a bridge will appear as a protrusion with a length close to that of the distance between the pins on the board with the gray level of the protrusion end being similar to the joint gray level. The rest of the protrusions will be considered spikes/icicles as long as the length and width meet a minimum criteria.

Solder ball defects typically appear spherical and may appear anywhere on the circuit board. Under the assumption the suspect solder ball has been found by previous algorithms the $0^{th}$, $1^{st}$ and $2^{nd}$ moments of the solder are calculated to obtain the length of the major and minor axes. If the ratio of the major and minor axes is within a tolerance of 1.0, the solder is considered somewhat symmetrical. Next the spherical area of the object is calculated by assuming the diameter (D) is the average of its major and minor axes by using formula $\pi(D/2)^2$. The ratio of this area to the $0^{th}$ moment is used in obtaining the spherocity (S). If the spherocity is within a tolerance of 1.0, the object is considered a solder ball. The setup for detecting this type of defect typically requires a large field of view without any tilt.

Another defect which may occur in a typical solder connection is excess solder in the bend radius where solder extends into the stress release bend of a horizontally mounted component. This defect may occur in all axial lead components at the bend radius. The setup requirements of the motion table typically require a 1 inch field of view, or less, with a 30 degree or greater tilt angle with no rotation. The theory behind this measurement and comparison algorithm is that solder in the bend radius will also appear on the back side of the bend radius. This defect can be described as a lump of solder on the back of the lead which will appear as a change in a bend angle of the lead. Instead of bending in toward the component body, the lump will make a slight bend away. In the algorithm, a search of the lead outside edge away from the component body is conducted so as to find the bend. The angle of the lead is then recorded. The angle is projected past the bend and the image is sampled for solder in the area where the lead would be. The defect exists if solder is found at the projected angle.

Another defect is where a bent or missing lead occurs such that the component lead has been bent so that the lead does not enter the hole, or the lead is completely missing. This algorithm is used in inspecting through-hole components on the insertion side of the board. Typical motion table setup requirements are a large field of view with no tilt. The theory in inspection for this defect is that the lead, having a lower density than solder, increases the standard deviation of the solder barrel. In determining the defect, the standard deviation of the barrel is calculated and if the standard deviation is below a threshold then a defect is determined to exist.

The surface mount defect known as a bent lead occurs when a lead is bent to one side within the plane of the device. In measuring this defect, a 1-inch field of view is required with no tilt angle. The measurement algorithm is performed by computing the centroid of the pin and the pad. The shift in the centroids of the pin and pad (A) are next measured. Next, the average shift over the row of pins (B) is calculated. A lead is bent if the absolute value of the average shift over the row of pins subtracted from the shift in centroids of the pin and pad is greater than a threshold, i.e. ABS (A—B)>threshold.

A cold pad defect is typically a "cold solder joint" which is a phrase generally describing a poor quality joint. This defect may show signs of dewetting, voids, cracks, or an unusual solder distribution. This defect may occur in through-hole devices on the top or bottom of the circuit board. The motion table setup requires a minimum field of view with a tilt sufficient to displace the upper and lower pads. The measurement algorithm utilizes the given pad centers and two limiting angles for pad examination. The radial symmetry factor of the joints are calculated by calculating the standard deviation along two arcs (A and B) such that the MAX (A,B)=C. If C is greater than a threshold then the defect exists.

Dewetting on the lead defect is a failure of the solder to completely stick to the lead and usually the solder is slightly pulled away from the lead. This defect typically occurs at the top and bottom of leads in throughhole components. The motion table setup typically requires a small field of view with a 30 degree or greater tilt angle, with multiple rotated views necessary to examine the entire lead circumference. Dewetting will typically appear as a blackish halo around the lead which indicates a higher density of solder. Instead of flowing evenly around the fillet, the solder has gathered into sections of higher and lower density. To determine whether dewetting has occurred, the barrel average gray level ($B_a$) is calculated. The average gray levels are recorded in three locations when scanning from the barrel up the lead toward the component. The position of the highest differential in gray levels of the white-to-black transition for each of the three scans is recorded. The average gray level of the arc defined by the three points of higher differentials of gray level is then computed as the value ($A_a$). If $A_a - B_a <$ threshold, then the dewetting defect exists.

Dewetting on the pad is a defect characterized by a jagged edge occuring at the circumference of the solder on the pad and may be found at top and bottom pad areas for through-hole components. In imaging this type of defect a small field of view with a 30 degree or greater tilt angle and multiple rotated views are necessary to examine the pad. Dewetting will appear as a white halo around the barrel which indicates a lower solder density. Instead of flowing evenly around the fillet, the solder has pulled away from the barrel thereby leaving a gap. This gap lowers the density so as to produce the white halo around the barrel. In measuring the defect, the barrel average gray level ($B_a$) is computed. The barrel is scanned out towards the pad edge at three locations with the average gray level recorded. The position of the highest differential in gray levels of the black-to-white transition for each of the three scans is recorded. The average gray level of the arc defined by the position of the highest differential in gray levels recorded is computed as value ($A_a$). If $A_a - B_a >$ threshold, then the dewetting on the pad defect exists.

Excess solder on the bottom lead is characterized by solder obscuring the end of the lead on the bottom side of the circuit board and typically occurs at circuit board bottom side pad area. The imaging for this type of defect typically requires a 1-inch field of view or less with a 30 degree or greater tilt angle. In the measurement of this type of defect, when the lightest gray level minus the barrel gray level is large the lead tip is clinched. This could mean that the pin is covered with solder or the lead was not clinched. Testing the difference between the pad gray level with the barrel gray level will indicate if the solder does cover the lead tip. When the solder covers the lead tip it also covers the pad more than normal. This covering of the pad with more than normal solder lowers the difference in gray level between the barrel and pad. In performing the measurement, the gray levels from the center of the barrel to the end of the bottom pad are sampled with the lightest gray level average ($G_1$) being recorded. The average gray level at the barrel center ($B_a$) and the average of the bottom pad gray level ($P_a$) are recorded. If the average of the bottom pad gray level subtracted from the lightest average gray level ($G_1 - B_a$) is less than a threshold, and the average gray level of the barrel center subtracted from the average gray level of the bottom pad ($P_a - B_a$) is less than a threshold, then the defect exists.

Excess solder on the top of the lead is characterized by solder on the lead surface above the top fillet. This defect typically occurs in the soldering of dual in-line packages, single in-line packages and through-hole devices. The imaging setup requirement for this type measurement is typically a 1-inch field of view at a 30-45 degree tilt angle. The measurement of the image data utilizes a given center position of the barrel wherein the average gray level of the barrel ($B_a$) is calculated. The data on the lead is extracted wherein between the knee and pad, the following are calculated: maximum standard deviation of the rows ($R_s$), maximum standard deviation of the columns ($C_s$), and the minimum gray level of population 2 or more ($M_1$). If the maximum standard deviation of the rows ($R_s$) or the maximum standard deviation of the columns ($C_s$) is greater than a threshold, then small solder globs exist on the lead. If the average gray level of the barrel subtracted from the minimum gray level ($M_1 - B_a$) < threshold, then the lead is covered with solder.

Excess solder on the pads occurs when solder extends beyond the edge of the pad and is considered a solder defect. This defect may occur in individual or paired top and bottom pads. In the measurement of the image for the defect, the approximate joint center location is given. If the measured diameter of the pad is greater than a threshold then a defect exists.

Insufficient lead clearance occurs when a clinched lead protrudes towards another lead so that the clearance between the two leads is less than a specified amount. This defect occurs only on the bottom side of through-hole components. The typical image measurement setup requires a large field of view with no tilt. In theory, the distance from the end of a lead to any other object can be defined from the nontilted position. Although the actual clearance may be larger due to the depth not being measured, the lead has the potential of being within the measured clearance if bent. In performing a measurement on the solder connection, a circular profile of pixel data around the joint pad is gathered, excluding any known device interference. The data is filtered using a median filter. A potential defect exists if the differential along the profile varies more than a threshold level. For potential defects, the angle of the defect from the position in the profile is calculated. The measurements are continued by scanning outwardly from the joint pad at the found angle, so as to follow the path of the lowest gray level until the gray level rises above a threshold, or a fixed distance is covered. Next, the measurements are taken by continuing to scan from the end out, straight and to both sides, for a distance equal to the specified clearance. If contact with a second lead is found then insufficient clearance exists.

In surface mount devices a defect may occur when the amount of solder volume between the pin and pad is insufficient. This test typically requires a 1-inch field of view with no tilt. In measuring the image, the approximate joint center location is given wherein the average gray level of a window on the joint is computed. If the average gray level is smaller than a threshold, then there is insufficient solder at the connection.

In all through-hole components insufficient solder at the top or bottom fillet occurs when solder fall-back into the barrel is more than a specified amount. Typically this measurement requires a field of view dependent upon the barrel dimensions with a large tilt angle. If a normal amount of solder exists on the pad, the fall-back into the barrel is acceptable. The fall-back is measured by testing whether solder is present at the maximum acceptable fall-back location. If the solder does not extend from one side of the barrel to the other, then the fall-back extends beyond this point and the joint is defective. In measuring the image, the average gray level of the pad is computed and recorded. If this computation shows a normal or more than normal amount of solder, then there is no defect. However, should this not be the case, the location where the barrel and pad meet is computed and recorded. At the point where fall-back becomes unacceptable, the width of the solder in the barrel is measured by utilizing the gray scale level. If the width is less than the barrel diameter, then a defect exists.

A lifted pin defect occurs when a pin is lifted up from the pad area which results in no bonding between the pin and pad. However, solder may still be present on the pin and pad. This defect typically occurs on surface mounted devices and flat pack components. The image measurement typically requires a 1-inch field of view with no tilt. In measuring the image the center locations on a row of joints are given. Inspection windows are placed about each pin and pad area so as to calculate the average gray level and the black counts for various thresholds. The results are then compared with thresholds to determine if a defect exists.

Through-hole component misorientation occurs when a component is improperly inserted into the circuit board. This defect typically requires a large field of view with no tilt to perform the image measurement. In theory the internal/external structure of a component varies enough so that when misoriented, the image is significantly different than when oriented properly. In performing the measurement on the image, the average gray level of a section of the component is calculated and normalized to a step wedge. If the average minus the expected average, corresponding to a properly aligned component, is not within a tolerance limit, then a defect exists.

A missing component is another typical defect which occurs when a component is absent from the circuit board. This measurement typically uses a large field of view without tilt. The density of the component will decrease the average gray level at the expected position on the board. For devices with low X-ray density, the gradient may yield a stronger signature. In the measurement, the expected location and size of the component is given. The average gray level of a section of a component that is significantly different in signal from the background is calculated. This signal is normalized with a step wedge and/or local background. If the average minus the expected average is not within a predetermined tolerance, then a defect exists. For low-density components an additional test may be required. This test requires that the maximum gradient across the expected component edges, where the solder joints are located, be measured. If this value is less than a threshold, then a defect exists.

A splash in an open area is a typical defect which occurs when amorphic solder globs are stuck to the circuit board in random locations. The defect may occur at all open areas on the circuit board. Measurement of the image for this type of defect requires a large field of view without a tilt. In measuring the image the average (A) and standard deviation ($S_d$) gray levels of the test zone are computed. The average gray level is normalized with calibration data ($N_a$). If the expected average subtracted from the calibration data ($N_a - A_b$) is greater than a threshold or the expected standard deviation subtracted from the measured standard deviation ($S_d - S_{de}$) is greater than a threshold, then a defect exists.

A blow-hole or a void is typically defined as a cavity on the top or bottom fillet which may occur on all throughhole component solder connections. The image measurement typically requires a field of view dependent upon the barrel dimensions with a large tilt angle. To cover all areas of the pad this test requires multiple views at different rotations. Voids and blow-holes typically cause small areas of low-density gray levels in the fillet image. In measuring the image, the minimum and maximum gray levels, of population 2 or more, of the fillet are calculated. If the difference between the minimum and maximum gray levels is less than a threshold then no defect exists. However, should the two gray levels difference exceed a threshold, the area of the potential defect is reexamined. The area of the potential defect is measured by using the black count at a gray level threshold set to a defined level above the minimum gray level. If this area is less than a threshold for a void/blow-hole, then a defect exists.

Upon reading of the previous description of the preferred embodiment, any person skilled in the art will readily understand how to make or use the present invention. Various modifications to these embodiments will be readily apparent to those skilled in the art, and the generic principles defined herein may be applied to other embodiments without the use of the inventive faculty. Thus, the present invention is not intended to be limited to the embodiment shown herein, but is to be accorded the widest scope consistent with the principles and novel features disclosed herein.

What is claimed is:

1. An apparatus for measuring structural characteristics of selected portions of a circuit board having components disposed upon and electrically connected thereto at solder joints, comprising:

X-ray means for providing a beam of X-rays;

multi-axis positioning means for receiving and for selectively positioning a circuit board, said circuit board having components coupled thereto at solder joints, within said beam of X-rays;

imaging means for detecting X-rays from said beam of X-rays transmitted through said circuit board and providing an electronic image thereof;

processing means for converting said electronic image into a gray scale coded image; and computational means for storing a library of measurement algorithms and predetermined measurement parameters corresponding thereto, for receiving said gray scale coded image, for analyzing said gray scale coded image by selecting measurement algorithms from said library of measurement algorithms with the selected measurement algorithms corresponding to certain structural characteristics of said circuit board, performing predetermined computational analysis on said gray scale coded image based upon each selected measurement algorithm, and providing a resultant analysis value corresponding to each computational analysis, for comparing each resultant analysis value with each corresponding measurement parameter, and for providing an output corresponding to the variation of each resultant analysis value from each corresponding predetermined measurement parameter.

2. The apparatus of claim 1 further comprising filter means for modifying the energy spectrum of X-rays in said beam of X-rays.

3. The apparatus of claim 1 wherein said imaging means comprises a solid state detector.

4. The apparatus of claim 1 wherein said imaging means comprises:

optical imaging means for providing an optical image corresponding to the intensity of X-rays transmitted through said circuit board; and electronic imaging means for converting said optical image into a corresponding electrical image.

5. The apparatus of claim 4 wherein said optical imaging means comprises a scintillating screen positioned to receive X-rays transmitted through said circuit board.

6. The apparatus of claim 4 wherein said electronic imaging means comprises:

a video camera;

and reflecting means mounted adjacent said video camera for reflecting said optical image from said optical imaging means to said video camera.

7. The apparatus of claim 1 wherein said processing means comprises a high-speed digital gray scale image processor.

8. The apparatus of claim 1 wherein said multi-axis positioning system comprises:

controller means responsive to instruction signals generated by said computational means for providing predetermined position signals; and motion table means responsive to said position signals for moving said circuit board mounted thereupon in x, y and z orthogonal axis with rotation in each axis.

9. The apparatus of claim 1 wherein said X-ray means comprises an electronic X-ray source.

10. The apparatus of claim 1 wherein said gray scale coded image generated by said processing means from said electronic image represents the radiographic density of said circuit board said beam of X-rays are transmitted therethrough.

11. The apparatus of claim 1 wherein said computational means further provides an output indication as to whether each resultant analysis value is within said corresponding predetermined measurement parameter.

12. The apparatus of claim 1 wherein said computational means provides said output as an output signal indicative of measurement data for the measured structural characteristics of a manufactured circuit board under test.

13. The apparatus of claim 1 wherein said computational means further provides visual display of said output of measurement data for the measured structural characteristics of said circuit board under test.

14. The apparatus of claim 1 wherein each selected measurement algorithm corresponds to a certain structural characteristic of a respective one of an electronic device, a mechanical device, an electrical component, and a mechanical component of said circuit board under test.

15. The apparatus of claim 14 wherein said computational means further provides an output indication as to whether each resultant analysis value is within said corresponding predetermined measurement parameter.

16. A method of determining the structural characteristics of a circuit board having components disposed thereupon and connected thereto at solder joints, comprising the steps of:

supporting a circuit board having certain structural characteristics by a multi-axis positioning means adjustable for optimum exposure of said circuit board to a source beam of X-rays;

exposing said circuit board to a beam of X-rays having sufficient energy to penetrate said circuit board;

detecting X-rays transmitted through said circuit board and providing an electronic image thereof;

coverting said electronic image into a gray scale coded image;

providing a library of measurement algorithms;

providing predetermined measurement parameters corresponding to said measurement algorithms;

selecting at least one measurement algorithm with each selected measurement algorithm corresponding to a respective one of said certain structural characteristics;

performing predetermined computational analysis on said gray scale coded image using each selected measurement algorithm;

providing a resultant analysis value corresponding to each computational analysis;

comparing each resultant analysis value with each corresponding predetermined measurement parameter; and providing an output indicative of the variation of each resultant analysis value from each corresponding predetermined measurement parameter.

17. The method of claim 16 further comprising the step of providing an output as an indication of whether each resultant analysis value is within said corresponding predetermined measurement parameter.

18. The method of claim 16 wherein said output includes quantitative data corresponding to the structural characteristics of at least one inspected circuit board component.

19. The method of claim 16 wherein the step of detecting includes:
   disposing a scintillating screen in the path of X-rays passing through said circuit board, said scintillating screen generating an optical image of X-rays passing through said circuit board;
   viewing said optical image generated by said scintillating screen with a video imaging system;
   providing an electronic signal corresponding to the optical image observed by said video imaging system.

20. The method of claim 16 wherein the step of performing predetermined computational analysis further comprises the steps of:
   selecting at least one measurement algorithm from a pre-structured library of measurement algorithms;
   controlling the detection of X-rays in accordance with said algorithms; and
   recording each resultant analysis value in an electronic storage means.

21. The method of claim 15 further comprising the step of providing an output indication whether each resultant analysis value is within said corresponding predetermined measurement parameter.

* * * * *